United States Patent
Hwang et al.

(10) Patent No.: US 11,731,093 B2
(45) Date of Patent: Aug. 22, 2023

(54) CATALYST LOADING METHOD AND METHOD FOR PREPARATION OF BUTADIENE BY USING SAME

(71) Applicant: LG CHEM, LTD., Seoul (KR)

(72) Inventors: Ye Seul Hwang, Daejeon (KR); Daeheung Choi, Daejeon (KR); Myungji Suh, Daejeon (KR); Sunhwan Hwang, Daejeon (KR); Dong Hyun Ko, Daejeon (KR); Kyong Yong Cha, Daejeon (KR); Jun Kyu Han, Daejeon (KR)

(73) Assignee: LG CHEM, LTD., Seoul (KR)

( * ) Notice: Subject to any disclaimer, the term of this patent is extended or adjusted under 35 U.S.C. 154(b) by 448 days.

(21) Appl. No.: 16/968,014

(22) PCT Filed: Jan. 29, 2019

(86) PCT No.: PCT/KR2019/001213
§ 371 (c)(1),
(2) Date: Aug. 6, 2020

(87) PCT Pub. No.: WO2019/160259
PCT Pub. Date: Aug. 22, 2019

(65) Prior Publication Data
US 2021/0362111 A1 Nov. 25, 2021

(30) Foreign Application Priority Data

Feb. 14, 2018 (KR) .......................... 10-2018-0018419

(51) Int. Cl.
| | | |
|---|---|---|
| *B01J 8/00* | (2006.01) | |
| *B01J 8/02* | (2006.01) | |
| *B01J 8/06* | (2006.01) | |
| *B01J 23/745* | (2006.01) | |
| *B01J 35/00* | (2006.01) | |
| *B01J 35/02* | (2006.01) | |
| *B01J 35/08* | (2006.01) | |
| *C07C 5/48* | (2006.01) | |

(52) U.S. Cl.
CPC .............. *B01J 8/001* (2013.01); *B01J 8/008* (2013.01); *B01J 8/0015* (2013.01); *B01J 8/0207* (2013.01); *B01J 8/06* (2013.01); *B01J 23/745* (2013.01); *B01J 35/0006* (2013.01); *B01J 35/023* (2013.01); *B01J 35/08* (2013.01); *C07C 5/48* (2013.01); *B01J 2208/0038* (2013.01); *B01J 2208/0053* (2013.01); *B01J 2208/00663* (2013.01); *B01J 2208/00805* (2013.01); *B01J 2208/025* (2013.01)

(58) Field of Classification Search
CPC .......... B01J 8/001; B01J 8/0015; B01J 8/008; B01J 8/0207; B01J 8/06; B01J 23/745; C07C 5/48
See application file for complete search history.

(56) References Cited

U.S. PATENT DOCUMENTS

| | | | |
|---|---|---|---|
| 4,332,972 A * | 6/1982 | Christmann | ............. C07C 5/56 585/443 |
| 6,593,269 B1 | 7/2003 | Rubini et al. | |
| 9,550,174 B2 * | 1/2017 | Kwon | .................... B01J 37/088 |
| 10,518,250 B2 * | 12/2019 | Choi | ..................... B01J 37/088 |
| 2006/0045825 A1 | 3/2006 | Dieterle et al. | |
| 2007/0155988 A1 | 7/2007 | Cremer et al. | |
| 2011/0004041 A1 | 1/2011 | Chung et al. | |
| 2014/0141965 A1 | 5/2014 | Xiong et al. | |
| 2014/0189817 A1 | 7/2014 | Branam et al. | |
| 2014/0200379 A1 | 7/2014 | Josch et al. | |
| 2016/0318829 A1 | 11/2016 | Gaertner et al. | |
| 2018/0050970 A1 | 2/2018 | Kimura et al. | |
| 2018/0214854 A1 | 8/2018 | Choi et al. | |

FOREIGN PATENT DOCUMENTS

| | | |
|---|---|---|
| CN | 101980992 A | 2/2011 |
| CN | 103071429 A | 5/2013 |
| CN | 103657536 A | 3/2014 |
| CN | 105582954 A | 5/2016 |
| EP | 3488921 A2 | 5/2019 |
| JP | 2011219366 A | 11/2011 |
| JP | 2012077074 A | 4/2012 |
| JP | 2014065674 A | 4/2014 |
| JP | 2016175888 A | 10/2016 |
| KR | 20000062434 A | 10/2000 |
| KR | 20070011581 A | 1/2007 |
| KR | 10-1340621 B1 | 12/2013 |
| KR | 20150092146 A | 8/2015 |
| KR | 20160098383 A | 8/2016 |
| KR | 20170103532 A | 9/2017 |

* cited by examiner

Primary Examiner — Yong L Chu
(74) Attorney, Agent, or Firm — Bryan Cave Leighton Paisner LLP

(57) ABSTRACT

The present specification relates to a method comprising: (A) mixing a ferrite-based catalyst molded article with diluent material particles; and (B) adding the mixture to a catalyst reactor, and a method for preparing butadiene using the same.

10 Claims, No Drawings

CATALYST LOADING METHOD AND METHOD FOR PREPARATION OF BUTADIENE BY USING SAME

The present application is a National Phase entry pursuant to 35 U.S.C. § 371 of International Application No. PCT/KR2019/001213 filed Jan. 29, 2019, and claims priority to and the benefit of Korean Patent Application No. 10-2018-0018419 filed in the Korean Intellectual Property Office on Feb. 14, 2018, the entire contents of which are incorporated herein by reference.

FIELD

The present specification relates to a method for filling a catalyst and a method for preparing butadiene using the same.

BACKGROUND 1,3-butadiene is an intermediate of petroleum chemical products, and demands for 1,3-butadiene, and the value thereof, are gradually increasing globally. 1,3-butadiene has been prepared by using naphtha cracking, the direct dehydrogenation reaction of butene, oxidative dehydrogenation reaction of butene, and the like.

The oxidative dehydrogenation reaction of butene is a reaction in which butene and oxygen react with each other in the presence of a metal oxide catalyst to produce 1,3-butadiene and water, and has a thermodynamically very favorable advantage because stable water is produced. Further, since the oxidative dehydrogenation reaction of butene is an exothermic reaction unlike the direct dehydrogenation reaction of butene, 1,3-butadiene may be obtained at high yield even at low reaction temperature as compared to the direct dehydrogenation reaction. The oxidative dehydrogenation reaction of butene may become an effective single production process capable of satisfying the demands for 1,3-butadiene because an additional heat supply is not required.

The metal oxide catalyst is generally synthesized by a precipitation method. In particular, when a ferrite-based catalyst is used as a metal oxide catalyst, the ferrite-based catalyst generates heats, thereby increasing the COx selectivity and decreasing the butadiene selectivity. Accordingly, studies on controlling exotherm and simultaneously controlling the hot spot movement of the catalyst have been continuously conducted.

SUMMARY

The present specification provides a method for filling a catalyst and a method for preparing butadiene using the same.

An exemplary embodiment of the present specification provides a method comprising:

(A) mixing a ferrite-based catalyst molded article with diluent material particles to form a mixture; and (B) adding the mixture of the ferrite-based catalyst molded article and the diluent material particles to a catalyst reactor.

Another exemplary embodiment of the present specification provides a method for preparing butadiene, the method comprising:

adding the mixture to a catalyst reactor according to the above-described method; and preparing butadiene by subjecting a raw material comprising butene to an oxidative dehydrogenation reaction in the catalyst reactor.

Further, an exemplary embodiment of the present specification provides a catalyst reactor which contains a mixture of a ferrite-based catalyst molded article and diluent material particles.

A method according to an exemplary embodiment of the present specification may simultaneously control a hot spot movement rate of a catalyst within a range capable of controlling exotherm caused by a catalyst reaction during an oxidative dehydrogenation reaction of butene, thereby securing the stability of the reaction and reducing costs caused by an increase in reaction temperature.

In addition, the hot spot movement rate may be decreased by controlling the concentration of a catalyst as compared to a diluent material in a section of a catalyst reactor where a reaction starts.

DETAILED DESCRIPTION

Hereinafter, the present specification will be described in more detail.

In the present specification, the 'yield (%)' is defined as a value obtained by dividing the weight of 1,3-butadiene as a product of an oxidative dehydrogenation reaction by the weight of butene (BE) as a raw material. For example, the yield may be represented by the following equation.

Yield (%)=[(the number of moles of 1,3-butadiene produced)/(the number of moles of butene supplied)]×100

In the present specification, the 'conversion rate (%)' refers to a rate at which a reactant is converted into a product, and for example, the conversion rate of butene may be defined by the following equation.

Conversion rate (%)=[(the number of moles of butene reacted)/(the number of moles of butene supplied)]×100

In the present specification, the 'selectivity (%)' is defined as a value obtained by dividing the change amount of butadiene by the change amount of butene. For example, the selectivity may be represented by the following equation.

Selectivity (%)=[(the number of moles of 1,3-butadiene or COx produced)/(the number of moles of butene reacted)]×100

In the present specification, the 'hot spot of a catalyst' means a place where the temperature on the catalyst is the highest in the reactor.

An exemplary embodiment of the present specification comprises: (A) mixing a ferrite-based catalyst molded article with diluent material particles; and (B) filling a catalyst reactor with a mixture of the ferrite-based catalyst molded article and the diluent material particles.

Further, an exemplary embodiment of the present specification provides a method for filling a catalyst, the method comprising filling at least a partial section in the catalyst reactor, such that the ratio of the weight of the ferrite-based catalyst molded article to the sum of the weights of the ferrite-based catalyst molded article and the diluent material particles is 10 wt % to 15 wt %.

A ferrite-based catalyst may be used in an oxidative dehydrogenation reaction of butene. The oxidative dehydrogenation reaction is an exothermic reaction, and an increase in COx selectivity and a decrease in butadiene selectivity occur due to the exotherm of the ferrite-based catalyst.

Accordingly, a technology of controlling exotherm by diluting the ferrite-based catalyst with an inactive material is known.

However, the related art has an effect of decreasing the amount of heat generated by a catalyst reaction, but as the reaction time elapses, there occurs a phenomenon in which a hot spot of the catalyst moves to the rear side of the reactor in a longitudinal direction, and the reaction temperature needs to be increased to maintain the position of the hot spot.

The movement of the hot spot of the catalyst is associated with the inactivity of the catalyst, and there is a problem in that the increase in reaction temperature causes an increase in process costs.

Accordingly, the present inventors could adjust the dilution ratio of a catalyst molded article in a catalyst reactor by using the catalyst reactor which is filled by mixing diluent material particles with the catalyst molded article instead of diluting the catalyst itself. As a result, the present inventors secured the stability of operation by simultaneously controlling the hot spot movement rate of a catalyst within a range capable of controlling exotherm caused by a catalyst reaction, and could reduce costs because the reaction temperature does not need to be increased. Further, the present inventors could reduce the hot spot movement rate by limiting the concentration of the catalyst in a section where an oxidative dehydrogenation reaction starts.

In addition, when a catalyst itself is diluted with a binder material and the like, the catalyst itself is embedded in the molded article, thereby significantly reducing a catalyst area in which an actual reactant may be brought into contact with the catalyst. However, since the method for filling a catalyst according to the present invention uses a catalyst molded article itself as it is, the surface of the catalyst introduced may be totally brought into contact with the reactant. Accordingly, the dilution ratio in the catalyst reactor may be easily adjusted to control the hot spot movement rate.

According to an exemplary embodiment of the present specification, the catalyst reactor may be filled with a ferrite-based catalyst molded article and diluent material particles, such that the dilution ratios of the top and the bottom in the catalyst reactor are different from each other.

According to an exemplary embodiment of the present specification, in at least a section in the catalyst reactor, the ratio of the weight of the ferrite-based catalyst molded article to the sum of the weights of the ferrite-based catalyst molded article and the diluent material particles may be 10 wt % to 15 wt %. Preferably, the ratio may be 10 wt % to 13 wt %. When the ratio of the weight of the catalyst molded article in at least a section in the catalyst reactor is within the above range, the hot spot movement rate of the catalyst may be decreased during the oxidative dehydrogenation reaction of butene.

In particular, according to an exemplary embodiment of the present specification, a section where a reaction in the catalyst reactor starts may be filled such that the ratio of the weight of the ferrite-based catalyst molded article to the sum of the weights of the ferrite-based catalyst molded article and the diluent material particles is 10 wt % to 15 wt %, and the entire section in the catalyst reactor may be filled, such that the ratio of the weight of the ferrite-based catalyst molded article as compared to the sum of the weights of the ferrite-based catalyst molded article and the diluent material particles is 10 wt % to 15 wt %. As described above, according to an exemplary embodiment of the present specification, the hot spot movement rate may be decreased by controlling the concentration of a catalyst as compared to a diluent material in a section of the catalyst reactor where a reaction starts.

According to an exemplary embodiment of the present specification, the section of the catalyst reactor where the reaction starts may mean the top of the reactor, that is, a section where a reactant of the oxidative dehydrogenation reaction flows in, and thus reacts in the presence of the catalyst. A section where the reaction terminates may mean the bottom of the reactor, that is, a bottom portion where the reactant of the oxidative dehydrogenation reaction has been flown down from the top after the reaction is completed.

According to an exemplary embodiment of the present specification, the entire section of the catalyst reactor may mean a region from a section of a catalyst reactor where a reaction starts to a section thereof where the reaction terminates, and specifically, may mean a region where the catalyst in the reactor is filled.

According to an exemplary embodiment of the present specification, from the section of the catalyst reactor where the reaction starts to the section thereof where the reaction terminates, the ratio of the weight of the ferrite-based catalyst molded article in the entire section may be uniform.

According to an exemplary embodiment of the present specification, the fact that the ratio of the weight of the ferrite-based catalyst molded article is made to be uniform may mean that the ratio of the weight of the ferrite-based catalyst molded article measured in any region in the catalyst reactor is the same.

According to an exemplary embodiment of the present specification, the ferrite-based catalyst may mean a ferrite-based catalyst prepared by a co-precipitation method. The co-precipitation method may comprise: co-precipitating a metal precursor and a basic aqueous solution; filtering a precipitate; drying the precipitate; and firing the precipitate.

In an exemplary embodiment of the present specification, the ferrite-based catalyst may be represented by the following Formula 1.

$$AFe_2O_4 \qquad \text{[Formula 1]}$$

In Formula 1, A is Cu, Ra, Ba, Sr, Ca, Cu, Be, Zn, Mg, Mn, Co, or Ni.

According to an exemplary embodiment of the present specification, the ferrite-based catalyst may be a zinc ferrite catalyst.

According to an exemplary embodiment of the present specification, the metal precursor may be a zinc precursor, a ferrite precursor, a manganese precursor, or the like, but is not limited thereto as long as the metal precursor is typically used. Further, the metal precursor may be one or more selected from the group consisting of nitrate, ammonium salt, sulfate, and chloride, or a hydrate thereof.

According to an exemplary embodiment of the present specification, when the ferrite-based catalyst is a zinc ferrite catalyst, the ferrite-based catalyst may be prepared by a co-precipitation method of bringing a zinc precursor and a ferrite-based precursor into contact with a basic aqueous solution.

According to an exemplary embodiment of the present specification, the zinc precursor may be zinc chloride ($ZnCl_2$).

According to an exemplary embodiment of the present specification, the ferrite-based precursor may be ferric chloride hydrate ($FeCl_3 \cdot 6H_2O$).

According to an exemplary embodiment of the present specification, a pH of the basic aqueous solution may be 7 to 11. Specifically, a pH of the basic aqueous solution may be more than 7 and 11 or less. More specifically, a pH of the basic aqueous solution may be 8 to 11. When the pH of the basic aqueous solution satisfies the above range, there is an effect of stably producing a metal composite catalyst.

According to an exemplary embodiment of the present specification, the basic aqueous solution may be one or more selected from the group consisting of potassium hydroxide, ammonium carbonate, ammonium bicarbonate, an aqueous sodium hydroxide solution, an aqueous sodium carbonate solution, and ammonium water. Preferably, the basic aqueous solution may be ammonia water.

According to an exemplary embodiment of the present specification, the drying of the precipitate may be performed before firing the precipitate, after the precipitate is filtered, and then subjected to a washing step.

According to an exemplary embodiment of the present specification, the drying of the precipitate may be performed in an oven at 80° C. to 150° C.

According to an exemplary embodiment of the present specification, the firing of the precipitate may be a step of increasing the temperature up to 650° C. at a rate of 1° C./min, and then firing the precipitate for 6 hours. The firing method may be a heat treatment method typically used in the art.

According to an exemplary embodiment of the present specification, the firing of the precipitate may be performed by injecting air at 1 L/min into a firing furnace.

According to an exemplary embodiment of the present specification, the ferrite-based catalyst may form a ferrite-based catalyst molded article by using an extruder.

According to an exemplary embodiment of the present specification, the ferrite-based catalyst molded article may be molded in the form of a pellet type, a ball type, or a hollow type.

According to an exemplary embodiment of the present specification, the pellet may have a diameter of 1 mm to 5 mm, or 1.5 mm to 3 mm. When the diameter of the pellet satisfies the above range, the exotherm of the catalyst may be controlled and the activity of the catalyst may be improved.

According to an exemplary embodiment of the present specification, a final ferrite-based catalyst molded article may be prepared by molding the ferrite-based catalyst into a pellet, and then sintering the ferrite-based catalyst.

According to an exemplary embodiment of the present specification, the diluent material particle may be a metal oxide. The metal oxide may be an oxide of one or more metals selected from the group consisting of zinc (Zn), ferrite (Fe), manganese (Mn), aluminum (Al), cobalt (Co), copper (Cu), radium (Ra), barium (Ba), strontium (Sr), calcium (Ca), and beryllium (Be), but is not limited thereto.

According to an exemplary embodiment of the present specification, the diluent material particle may be an aluminum oxide.

According to an exemplary embodiment of the present specification, the diluent material particle may be alpha aluminum oxide ($\alpha$-$Al_2O_3$).

According to an exemplary embodiment of the present specification, the diluent material particle may be a ball type having a diameter of 1 mm to 5 mm, or a ball type having a diameter of 2 mm to 3 mm. When the diameter of the diluent material particles satisfies the above range, the catalyst may be diluted at a desired ratio without hindering the activity of the catalyst during the mixing of the catalyst molded article, so that it is possible to decrease the hot spot movement rate of the catalyst. The diluent material particle may be not only a ball type, but other various types.

According to an exemplary embodiment of the present specification, the step (A) may comprise mixing 15 cc to 25 cc of the catalyst molded article with 120 cc to 140 cc of the diluent material particles.

According to an exemplary embodiment of the present specification, when the content of the catalyst molded article and the diluent material particles is within the above range, at the time of filling the catalyst reactor with the catalyst molded article and the diluent material particles, the content may be adjusted, such that the ratio of the weight of the catalyst molded article to the total weight of the catalyst molded article mixed with the diluent material particles is 10 wt % to 15 wt %.

Another exemplary embodiment of the present specification provides a method for preparing butadiene, the method comprising: filling a catalyst reactor with a catalyst according to the above-described method for filling a catalyst; and preparing butadiene by subjecting a raw material comprising butene to oxidative dehydrogenation reaction in the catalyst reactor.

According to an exemplary embodiment of the present specification, the hot spot movement rate of the catalyst of the oxidative dehydrogenation reaction may be 0 to 0.5 mm/hr, 0.00001 mm/hr to 0.3 mm/hr, or 0.01 mm/hr or more and less than 0.2 mm/hr. The movement of the hot spot of the catalyst is associated with the inactivity of the catalyst, and the increase in reaction temperature may incur a problem in that an increase in process costs is caused. Accordingly, according to an exemplary embodiment of the present specification, when the hot spot movement rate of the catalyst of the oxidative dehydrogenation reaction satisfies the above numerical range, it is possible to obtain an effect of reducing operation costs due to the low inactivity rate of the catalyst.

Further, an exemplary embodiment of the present specification provides a catalyst reactor which is filled with a mixture of a ferrite-based catalyst molded article and diluent material particles.

In addition, an exemplary embodiment of the present specification provides a catalyst reactor in which the ratio of the weight of the catalyst molded article to the total weight of the catalyst molded article mixed with the diluent material particles is 10 wt % to 15 wt % in at least a section in the catalyst reactor.

According to an exemplary embodiment of the present specification, the ratio of the weight of the catalyst molded article to the total weight of the catalyst molded article mixed with the diluent material particles may be 10 wt % to 13 wt %.

In particular, according to an exemplary embodiment of the present specification, in a section where a reaction in the catalyst reactor starts, the ratio of the weight of the ferrite-based catalyst molded article to the sum of the weights of the ferrite-based catalyst molded article and the diluent material particles may be 10 wt % to 15 wt %, and in the entire section in the catalyst reactor, the ratio of the weight of the ferrite-based catalyst molded article to the sum of the weights of the ferrite-based catalyst molded article and the diluent material particles may be 10 wt % to 15 wt %. When the ratio of the weight of the catalyst molded article in the entire section of the catalyst reactor is within the above range, the hot spot movement rate of the catalyst may be decreased during the oxidative dehydrogenation reaction of butene.

Furthermore, another exemplary embodiment of the present specification provides a method for preparing butadiene, the method comprising preparing butadiene by subjecting a raw material comprising butene to oxidative dehydrogenation reaction in the above-described catalyst reactor.

According to an exemplary embodiment of the present specification, the preparing of the butadiene may use a reactant comprising a $C_4$ mixture. The $C_4$ mixture comprises one or more normal butenes selected from 2-butene (trans-2-butene, cis-2-butene) and 1-butene as an example, and selectively, may further comprise normal butane or $C_4$ raffinate-3. The reactant may further comprise one or more selected from air, nitrogen, steam, and carbon dioxide as an example, and preferably, further comprises nitrogen and steam. As a specific example, the reactant may comprise the $C_4$ mixture, oxygen, steam, and nitrogen at a mol ratio of 1:0.1 to 1.5:1 to 15:0.5 to 10 or 1:0.5 to 1.2:5 to 12:0.5 to 5. Furthermore, the method for preparing butadiene according to an exemplary embodiment of the present specification has an advantage in that the reaction efficiency is excellent and waste water is generated in a small amount even though steam is used in a small amount of 1 to 10 or 5 to 10 mol based on 1 mol of the $C_4$ mixture, and ultimately provides an effect of reducing not only waste water treatment costs, but also energy consumed for the process. The oxidative dehydrogenation reaction may be performed, for example, at a reaction temperature of 250 to 500° C., 300 to 450° C., 320 to 400° C., 330 to 380° C., or 350 to 370° C., and within this range, the reaction efficiency is excellent without significantly increasing the energy costs, so that 1,3-butadiene may be provided with high productivity.

According to an exemplary embodiment of the present specification, the preparing of the butadiene is performed under conditions of a reaction temperature of 360° C. and a gas hourly space velocity (GHSV) of 120 $h^{-1}$ in a single reactor, and the reactant may comprise the $C_4$ mixture:oxygen:steam:nitrogen at a mol ratio of 1:0.67:5:2.67.

As described above, the method for filling a catalyst according to an exemplary embodiment of the present specification may fill a catalyst by mixing a ferrite-based catalyst molded article used for an oxidative dehydrogenation reaction with diluent material particles and constantly adjust the ratio of the weight of the catalyst molded article to the total weight of the catalyst molded article mixed with the diluent material particles in the entire section of the catalyst reactor, thereby controlling exotherm and simultaneously decreasing the hot spot movement rate of the catalyst.

EXAMPLES

Hereinafter, the present specification will be described in detail with reference to Examples for specifically describing the present specification. However, the Examples according to the present specification may be modified in various forms, and it is not interpreted that the scope of the present specification is limited to the Examples described below in detail. The Examples of the present specification are provided to more completely explain the present specification to a person with ordinary skill in the art.

EXAMPLES

<Preparation Example> Preparation of Catalyst

1) Preparation of Metal Oxide

A metal precursor solution was prepared by dissolving 12.019 g of zinc chloride ($ZnCl_2$) and 47.662 g of ferric chloride ($FeCl_3$) in 155.59 g of distilled water. In this case, for a mol ratio of the metal components comprised in the metal precursor solution, Zn:Fe=1:2. An aqueous ammonia solution was added dropwise to the prepared aqueous metal precursor solution such that the pH was 9, and the resulting mixture was stirred for 1 hour and co-precipitated. Thereafter, a co-precipitate was obtained by filtering the co-precipitation solution under reduced pressure, and after the co-precipitate was dried at 90° C. for 16 hours, the temperature was increased up to 650° C. from 80° C. at a warming rate of 1° C./min under an air atmosphere, a zinc-iron oxide ($ZnFe_2O_4$) powder having a spinel structure was prepared by maintaining the temperature for 6 hours.

2) Preparation of Pellet Catalyst for Oxidative Dehydrogenation Reaction

After the prepared metal oxide powder was ground to 0.6 mm to 0.85 mm, a mixture of isopropyl alcohol with water as a liquid binder was introduced into the powder, and then the resulting product was uniformly kneaded by using a kneader, and the kneaded product was molded into a cylindrical pellet having a diameter of 1.5 mm to 3 mm, a circular cross section, and a height of 1.5 mm to 9 mm by using an extrusion molding machine. The molded pellet was dried at 90° C. for 12 hours and heat-treated at 500° C. for 4 hours.

Example 1

130 cc of an $\alpha$-$Al_2O_3$ ball having a diameter of 2 mm to 3 mm was mixed with 20 cc of the ferrite-based catalyst molded article prepared in Preparation Example 1, and a reactor was filled with the mixture, such that the ratio of the catalyst molded article was 10.17 wt % in the entire section of the reactor.

Example 2

125 cc of an $\alpha$-$Al_2O_3$ ball having a diameter of 2 mm to 3 mm was mixed with 25 cc of the ferrite-based catalyst molded article prepared in Preparation Example 1, and a reactor was filled with the mixture, such that the ratio of the catalyst molded article was 13.00 wt % in the entire section of the reactor.

Example 3

The reactor was filled with 20 cc of the ferrite-based catalyst molded article prepared in Preparation Example 1 and 130 cc of the $\alpha$-$Al_2O_3$ ball having a diameter of 2 mm to 3 mm by varying the ratio of the top and the bottom of the reactor as in the following Table 1. In this case, the ratio of the catalyst in a section (top) of the reactor where the reaction started was 3.65 wt %.

TABLE 1

| Reactor | Catalyst (cc) | $\alpha$-$Al_2O_3$ (cc) |
|---|---|---|
| 1 (Top) | 0.33 | 13 |
| 2 | 0.33 | 13 |
| 3 | 0.67 | 13 |
| 4 | 0.67 | 13 |
| 5 | 1 | 13 |
| 6 | 2 | 13 |
| 7 | 3 | 13 |
| 8 | 4 | 13 |
| 9 | 4 | 13 |
| 10 (Bottom) | 4 | 13 |

Example 4

105 cc of an $\alpha$-$Al_2O_3$ ball having a diameter of 2 mm to 3 mm was mixed with 45 cc of the ferrite-based catalyst molded article prepared in Preparation Example 1, and a reactor was filled with the mixture, such that the ratio of the catalyst molded article was 25 wt % in the entire section of the reactor.

Comparative Example 1

After 2) the preparation of the catalyst for an oxidative dehydrogenation reaction in Preparation Example 1, 180 g of a commercially available alumina silicate support was coated with 17.8 g of the catalyst to mold the resulting product such that the ratio of the catalyst to the total weight of the ferrite-based catalyst molded article was 9 wt %.

A reactor was filled with 150 cc of the obtained ferrite-based catalyst molded article without any additional dilution.

Comparative Example 2

The entire section of the reactor was filled with the catalyst molded article without mixing 150 cc of the ferrite-based catalyst molded article prepared in Preparation Example 1 with a diluent material.

Experimental Example

The results of subjecting a raw material comprising butene to oxidative dehydrogenation reaction in each of the reactors in Examples 1 to 4 and Comparative Examples 1 and 2, and measuring the hot spot movement rate, the conversion rate of butene, the butadiene selectivity, the COx selectivity, and the change in temperature of the hot spot are shown in the following Table 2.

The preparing of the butadiene by the oxidative dehydrogenation reaction was performed under conditions of a reaction temperature of 360° C. and a gas hourly space velocity (GHSV) of 120 h$^{-1}$ in a single reactor, and the reactant comprised the $C_4$ mixture oxygen:steam:nitrogen at a mol ratio of 1:0.67:5:2.67.

the hot spot movement rate is decreased to 8/100 or less, and the conversion rate of butene is improved as compared to Comparative Example 1 in which a catalyst molded article diluted by coating a support with the catalyst itself is used.

In addition, when Example 1 is compared with Comparative Example 2, it can be confirmed that in Example 1 in which the catalyst molded article is used as it is and the ratio of the catalyst of the reactor is adjusted by using the diluent material particles, the hot spot movement rate is decreased to ½ or less as compared to Comparative Example 2 in which a catalyst which is not mixed with a diluent material is used.

When Example 1 is compared with Examples 3 and 4, it can be seen that when the reactor is filled such that the ratio of the catalyst in the section where the reaction starts is 10 wt % to 15 wt %, a better effect can be obtained.

Consequently, the method for filling a catalyst according to the present specification may ultimately decrease the hot spot movement rate of the catalyst by adjusting the ratio of the catalyst to a specific ratio in the entire section of the catalyst reactor where the oxidative dehydrogenation reaction occurs, particularly, a section where the reaction starts.

Although the preferred exemplary embodiments of the present invention have been described above, the present invention is not limited thereto, and various modifications can be made and carried out within the scope of the claims and the detailed description of the invention, and also fall within the scope of the invention.

The invention claimed is:

1. A method of feeding a catalyst reactor for preparation of butadiene comprising:
    (A) mixing a ferrite-based catalyst molded article with diluent material particles to form a mixture, wherein the ferrite-based catalyst is a zinc ferrite and the diluent particles are α-$Al_2O_3$; and
    (B) adding the mixture of the ferrite-based catalyst molded article and the diluent material particles to a catalyst reactor.

TABLE 2

| Classification | Ratio of catalyst in the section where the reaction starts (wt %) | Hot spot movement rate (mm/hr) | | Butene conversion rate (%) | Butadiene selectivity (%) | COx selectivity (%) | Hot spot temperature (° C.) |
|---|---|---|---|---|---|---|---|
| Example 1 | 10.17 | 4 mm/ 38.26 hr | 0.10 | 81.7 | 84.2 | 13.9 | 511 |
| Example 2 | 13.00 | 2 mm/ 15.05 hr | 0.13 | 80.4 | 85.1 | 13.4 | 513 |
| Example 3 | 3.65 | 20 mm/ 38.62 hr | 0.52 | 88.2 | 86.3 | 11.8 | 458 |
| Example 4 | 25 | 14 mm/ 28.60 hr | 0.49 | 77.2 | 83.7 | 13.9 | 525 |
| Comparative Example 1 | 9.00 | 12 mm/ 9.59 hr | 1.25 | 69.5 | 89.4 | 8.5 | 437 |
| Comparative Example 2 | 100.00 | 10 mm/ 49.21 hr | 0.20 | 76.2 | 81.5 | 16.1 | 571 |

According to Table 2, it can be confirmed that in the case of an oxidative dehydrogenation reaction of butene in a catalyst reactor which is filled with a mixture of the catalyst molded article with the diluent material particles according to Example 1, the hot spot movement rate is decreased.

When Example 1 is compared with Comparative Example 1, it can be confirmed that in Example 1 in which the catalyst molded article is used as it is and the ratio of the catalyst of the reactor is adjusted by using the diluent material particles, 2. The method of claim 1, wherein at least a section in the catalyst reactor is filled, such that a ratio of a weight of the ferrite-based catalyst molded article to a sum of the weights of the ferrite-based catalyst molded article and the diluent material particles is 10 wt % to 15 wt %.

3. The method of claim 2, wherein a section of the catalyst reactor where the reaction starts is filled, such that the ratio of the weight of the ferrite-based catalyst molded article as compared to the sum of the weights of the ferrite-based catalyst molded article and the diluent material particles is 10 wt % to 15 wt %.

4. The method of claim 2, wherein an entire section of the catalyst reactor is filled, such that the ratio of the weight of the ferrite-based catalyst molded article to the sum of the weights of the ferrite-based catalyst molded article and the diluent material particles is 10 wt % to 15 wt %.

5. The method of claim 1, wherein the ferrite-based catalyst molded article is molded in a form of a pellet type, a ball type, or a hollow type.

6. The method of claim 5, wherein the ferrite-based catalyst molded article is molded in a form of a pellet type, and the pellet has a diameter of 1 mm to 5 mm.

7. The method of claim 1, wherein the diluent material particle is a ball type having a diameter of 1 mm to 5 mm.

8. The method of claim 1, further comprising:
preparing butadiene by subjecting a raw material comprising butene to an oxidative dehydrogenation reaction in the catalyst reactor.

9. The method of claim 8, wherein a hot spot movement rate of the catalyst of the oxidative dehydrogenation reaction is 0 to 0.5 mm/hr.

10. The method of claim 1, further comprising forming the ferrite-based catalyst molded article, the forming comprising: preparing a powder comprising zinc ferrite, molding the powder to form a molded zinc ferrite body, and sintering the molded zinc ferrite body to form the ferrite-based catalyst molded article; and
wherein the diluent particles are mixed with the ferrite-based catalyst molded article subsequent to the forming.

* * * * *